(12) United States Patent
Komp (10) Patent No.: US 11,045,075 B2
(45) Date of Patent: Jun. 29, 2021

(54) SYSTEM AND METHOD FOR GENERATING A THREE-DIMENSIONAL MODEL OF A SURGICAL SITE

(71) Applicant: COVIDIEN LP, Mansfield, MA (US)

(72) Inventor: John W. Komp, Dillon, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 16/682,285

(22) Filed: Nov. 13, 2019

(65) Prior Publication Data

US 2020/0178774 A1     Jun. 11, 2020

Related U.S. Application Data

(60) Provisional application No. 62/777,623, filed on Dec. 10, 2018.

(51) Int. Cl.

| A61B 1/00 | (2006.01) |
| A61B 1/267 | (2006.01) |
| A61B 1/31 | (2006.01) |
| G06T 17/00 | (2006.01) |
| G06T 19/00 | (2011.01) |
| G06T 7/11 | (2017.01) |
| G16H 30/40 | (2018.01) |

(52) U.S. Cl.
CPC ...... *A61B 1/00172* (2013.01); *A61B 1/00009* (2013.01); *G06T 7/11* (2017.01); *G06T 17/00* (2013.01); *G06T 19/003* (2013.01); *G16H 30/40* (2018.01); *G06T 2200/08* (2013.01)

(58) Field of Classification Search
USPC ........................................................ 382/154
See application file for complete search history.

(56) References Cited

U.S. PATENT DOCUMENTS

| 5,687,737 | A | 11/1997 | Branham et al. |
| 7,474,407 | B2 | 1/2009 | Gutin |
| 7,538,859 | B2 | 5/2009 | Tearney et al. |
| 7,559,895 | B2 | 7/2009 | Stetten et al. |
| 7,756,305 | B2 | 7/2010 | Price |
| 7,857,756 | B2 | 12/2010 | Warren et al. |

(Continued)

FOREIGN PATENT DOCUMENTS

| EP | 2548495 A1 | 1/2013 |
| WO | 2019202827 A1 | 10/2019 |

OTHER PUBLICATIONS

Extended European Search Report issued in European Patent Application No. 19214381.6 dated Apr. 22, 2020.

*Primary Examiner* — Patricia I Young
(74) *Attorney, Agent, or Firm* — Weber Rosselli & Cannon LLP (57) ABSTRACT

A system for generating a 3D model of a surgical site includes a 3D endoscope and a computing device coupled to the 3D endoscope. The 3D endoscope includes a scanner for scanning a surface of a surgical site and a camera source for generating images of the surgical site. A 3D model of the surgical site, including objects therein, is generated using scan data and image data. The 3D model is updated by detecting a change in the surgical site, isolating a region of the surgical site where the change is detected, generating second scan data by scanning the surface of the isolated region, and updating the 3D model generated using the second scan data of the surface of the isolated region.

17 Claims, 6 Drawing Sheets

(56) References Cited

U.S. PATENT DOCUMENTS

| | | |
|---|---|---|
| 7,949,385 B2 | 5/2011 | Khamene et al. |
| 7,952,718 B2 | 5/2011 | Li et al. |
| 8,335,557 B2 | 12/2012 | Maschke |
| 8,382,662 B2 | 2/2013 | Soper et al. |
| 8,384,909 B2 | 2/2013 | Yun et al. |
| 8,460,195 B2 | 6/2013 | Courtney et al. |
| 8,494,794 B2 | 7/2013 | Dutta et al. |
| 8,784,321 B2 | 7/2014 | Courtney et al. |
| 8,983,580 B2 | 3/2015 | Boppart et al. |
| 9,375,133 B2 | 6/2016 | Kitamura et al. |
| 9,398,936 B2 | 7/2016 | Razzaque et al. |
| 9,554,774 B2 | 1/2017 | Moore et al. |
| 9,861,338 B2 | 1/2018 | Kanade et al. |
| 10,391,277 B2 | 8/2019 | Rahimian et al. |
| 2013/0131505 A1 | 5/2013 | Daon et al. |
| 2020/0015907 A1* | 1/2020 | Scheib ............... A61B 17/0482 |

* cited by examiner

SYSTEM AND METHOD FOR GENERATING A THREE-DIMENSIONAL MODEL OF A SURGICAL SITE

CROSS-REFERENCE TO RELATED APPLICATION

This application claims the benefit of and priority to U.S. Provisional Patent Application No. 62/777,623 filed Dec. 10, 2018, the entire disclosure of which is incorporated by reference herein.

BACKGROUND

Technical Field

The disclosure relates to surgical systems, and more particularly, to systems and methods of performing endoscopic thoracic imaging and treatment and generating three-dimensional (3D) models of a surgical site and objects therein.

Description of Related Art

Current monocular optical devices (e.g. endoscope, bronchoscope, colonoscope) used for viewing surgical fields during minimally invasive surgery (e.g. laparoscopy) and visual diagnostic procedures (e.g. colonoscopy, bronchoscopy) provide limited reference information on the absolute position of surgical tools and anatomical features because the image has no depth of field. To compensate, surgeons may advance the surgical tool until it comes in contact with a feature or another tool. This leads to inefficient motion and the potential for perforation of critical anatomical structures. Binocular (also known as stereoscopic) optical devices provide limited depth of field affording the surgeon visual information on the distance between-items within the optical device's field of view. The accuracy of distance information is limited based on the amount of parallax provided by the optical paths, determined by the distance between the optical paths, and the amount of overlap between the two optical paths.

SUMMARY

The disclosure relates to surgical systems, and more particularly, to systems and methods of generating 3D models of a surgical site and objects therein and generating or adjusting 3D models to compensate for movement of objects, such as tools or the anatomy, in the surgical site.

In an aspect, a method for generating a 3D model of a surgical site is provided. The method includes generating first scan data based on reflected IR projections projected onto a surface of the surgical site using a scanner and a camera source and generating a 3D model of the surgical site using the first scan data and image data of the surgical site. The method further includes detecting a change in the surgical site, isolating a region of the surgical site where the change is detected, generating second scan data of the isolated region based on reflected IR projections projected onto the isolated region using the scanner and the camera source, updating the 3D model generated using the second scan data of the surface of the isolated region, and displaying the updated 3D model on a display.

Detecting a change in the surgical site may include detecting movement of an object in the surgical site. In an aspect, detecting a change in the surgical site includes comparing an image of a portion of the surgical site captured by the camera source at a time t with an image of the portion of the surgical site captured by the camera source at a time t−1, and determining that there exists a change in the surgical site when the image captured at time t is different from the image captured at time t−1. Additionally, or alternatively, detecting a change in the surgical site includes comparing scan data of a portion of the surgical site at a time t with scan data of the portion of the surgical site at a time t−1, and determining that there exists a change in the surgical site when the scan data at time t is different from the scan data at time t−1.

In an aspect, generating first scan data based on reflected IR projections projected onto a surface of the surgical site using a scanner and a camera source includes using a scanner and a camera source of a 3D endoscope.

Generating second scan data of the isolated region based on reflected IR projections projected onto the isolated region using the scanner and the camera source may include reducing a field of view of the scanner. In an aspect, generating a 3D model of the surgical site using the first scan data and the image data includes warping the image data onto the first scan data.

In an aspect, the method further includes displaying the 3D model with portions of the 3D model corresponding to the isolated region flattened.

In yet another aspect of the disclosure, a system for generating a 3D model of a surgical site is provided. The system includes a 3D endoscope and a computing device operably coupled to the 3D endoscope. The 3D endoscope includes a camera source and a scanner. The computing device is configured to generate a 3D model of a surgical site using scan data and image data acquired by the 3D endoscope, detect a change in the surgical site, isolate a region of the surgical site where the change is detected, cause the scanner to scan a surface of the isolated region to generate second scan data of the isolated region, and update the 3D model generated using the second scan data of the isolated region.

In an aspect, the computing device is further configured to display, on a graphic user interface, the 3D model with portions of the 3D model corresponding to the isolated region flattened and display the updated 3D model.

The computing device may detect a change in the surgical site by detecting movement of an object in the surgical site. Additionally, or alternatively, the computing device detects a change in the surgical site by comparing an image of a portion of the surgical site captured by the camera source at a time t with an image of the portion of the surgical site captured by the camera source at a time t−1, and determining that there exists a change in the surgical site when the image captured at time t is different from the image captured at time t−1. In an aspect, the computing device detects a change in the surgical site by comparing scan data of a portion of the surgical site at a time t with scan data of the portion of the surgical site at a time t−1, and determining that there exists a change in the surgical site if the scan data at time t is different from the scan data at time t−1.

The computing device may scan the surface of the isolated region using the scanner to generate second scan data by reducing a field of view of the scanner. Additionally, or alternatively, the computing device generates the 3D model of the surgical site by warping the image data onto the first scan data. In an aspect, the 3D model includes a matrix of equidistant data points representing fixed points in a current view of the surgical site and a value of a data point represents an existence of an object at the data point in space.

In yet another aspect of the disclosure, a non-transitory computer-readable storage medium is provided. The non-transitory computer-readable storage medium is encoded with a program that, when executed by a processor, performs the steps of any of the methods described herein. In an aspect, the non-transitory computer-readable storage medium is encoded with a program that, when executed by a processor, causes the processor to generate a 3D model of a surgical site using scan data and image data, scan a surface of an isolated region of the surgical site corresponding to a portion of the surgical site that has changed to generate second scan data, and update the 3D model generated using the second scan data.

In an aspect, the non-transitory computer-readable storage medium is encoded with a program that, when executed by a processor, further causes the processor to detect a change in the surgical site by detecting movement of an object in the surgical site. Additionally, or alternatively, detecting a change in the surgical site may include comparing an image of a portion of the surgical site captured by a camera source at a time t with an image of the portion of the surgical site captured by the camera source at a time t−1, and determining that there exists a change in the surgical site when the image captured at time t is different from the image captured at time t−1. In an aspect, detecting a change in the surgical site may include comparing scan data of a portion of the surgical site at a time t with scan data of the portion of the surgical site at a time t−1, and determining that there exists a change in the surgical site if the scan data at time t is different from the scan data at a time t−1.

BRIEF DESCRIPTION OF THE DRAWINGS

Various aspects and features of the disclosure are described hereinbelow with references to the drawings, wherein.

DETAILED DESCRIPTION

In accordance with the disclosure, and as described in greater detail below, one method to create a true 3D map of a surface of a surgical site (e.g., a 3D model) is to use a scanner, which draws a pattern across the surface of the surgical site (e.g., IR projections), while capturing images of the surgical site (including the scanned surface) to generate scan data. For example, the scan data may be generated by analyzing the distortion of the images from reflections of IR projections projected by the scanner. The distortions in the captured images can be used to extract depth information to create the 3D map (e.g., 3D model). When the surface being scanned, or an object in the surgical site, moves more rapidly than the scan time, the resulting 3D equivalent (e.g., portion of the 3D model corresponding to the moving surface or object) is inaccurate and may appear similar to a blurred photograph.

To overcome this issue and increase the apparent scanning time of a three-dimensional imaging endoscope (3D endoscope), as described in detail below, it is advantageous to restrict the size of the scanning field to only those areas that have changed since the previous scan. In accordance with the disclosure, an initial scan is performed along with a capture of an image of the current field of view. Continuous images are captured and compared to the most recent (previous) image looking for a change (e.g. the image taken at time t will be compared to that taken at time t−1). Where a change is detected, a modified rescan is performed, where the modified rescan is restricted to the changed areas. Should the area of change between two consecutive images exceed what can be scanned without notice by the user, the 3D model is flattened in the changed area(s) until such time that a scan of the area can be completed, and the 3D model can be updated. This prevents loss of visual context during the update scan.

One aspect of the disclosure is directed to a 3D endoscope and systems that support organ matching to preoperative images, for example images of a lung, other anatomy or anatomical features within a surgical site. The 3D endoscope can provide both visual imaging and also surface mapping and is used to generate a 3D model by the 3D endoscope, by another component of the system such as a computing device, or by a combination of the 3D endoscope and the computing device.

Figure 1:
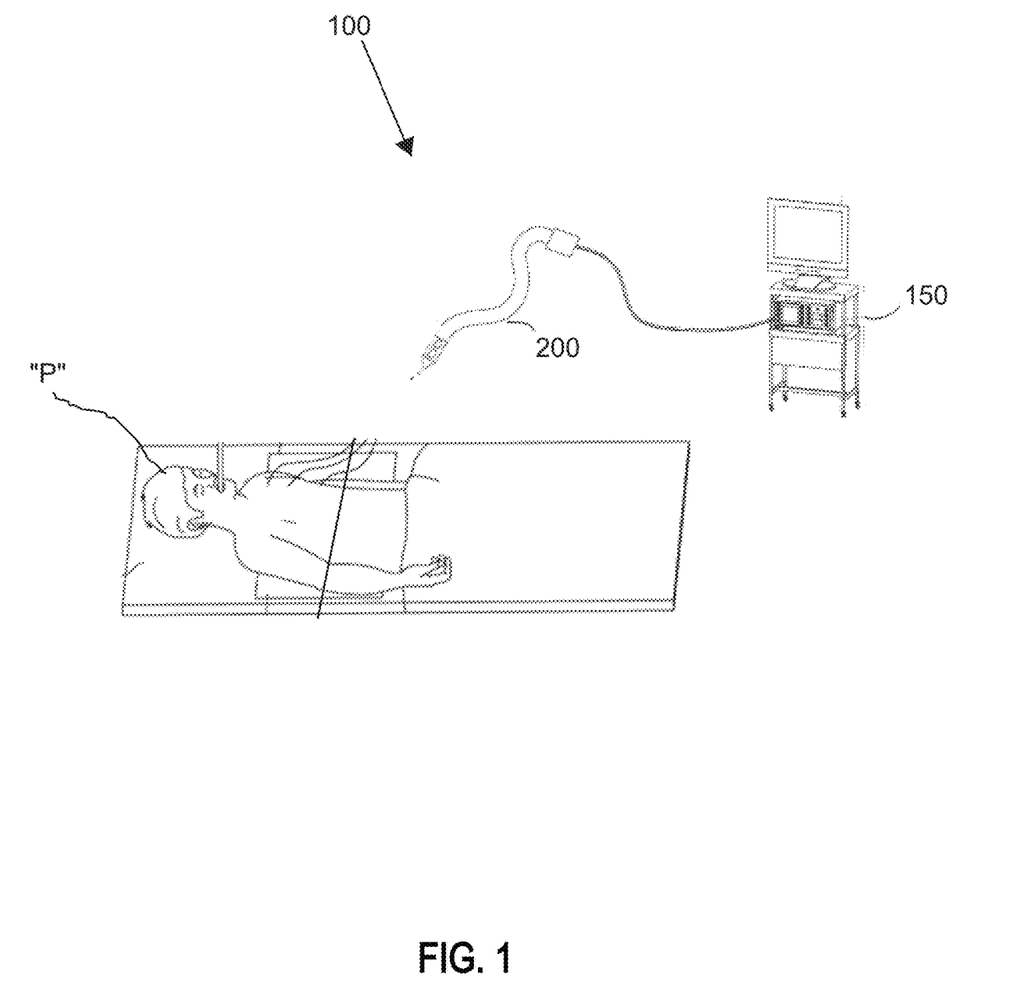
FIG. 1 is a schematic illustration of a surgical imaging system including a 3D endoscope and a computing device in accordance with the disclosure.
Figure 2:
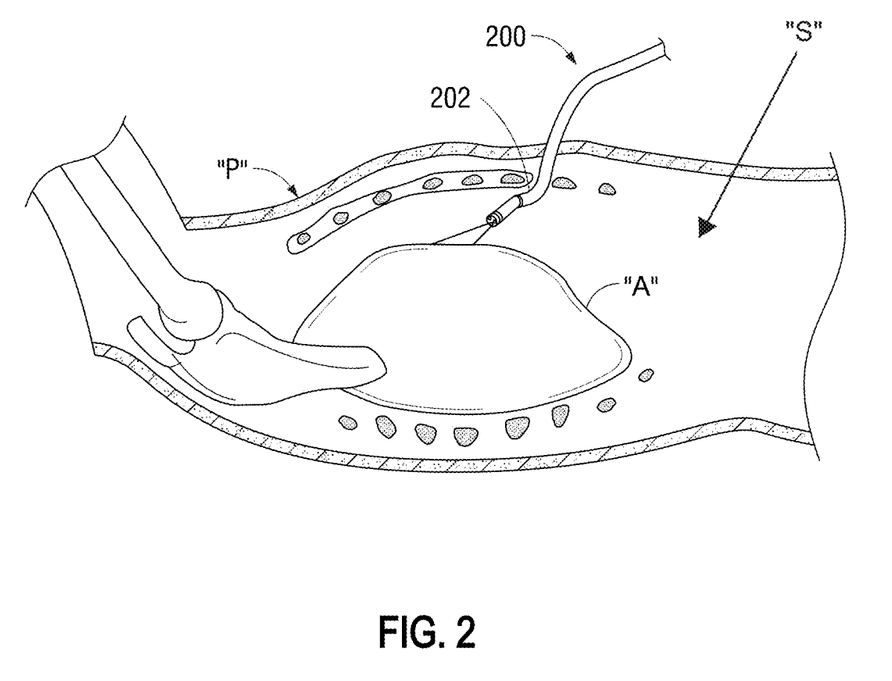
FIG. 2 is a side, cross-sectional view of the thoracic cavity of a patient with the 3D endoscope of FIG. 1 advanced therein.
Figure 3:
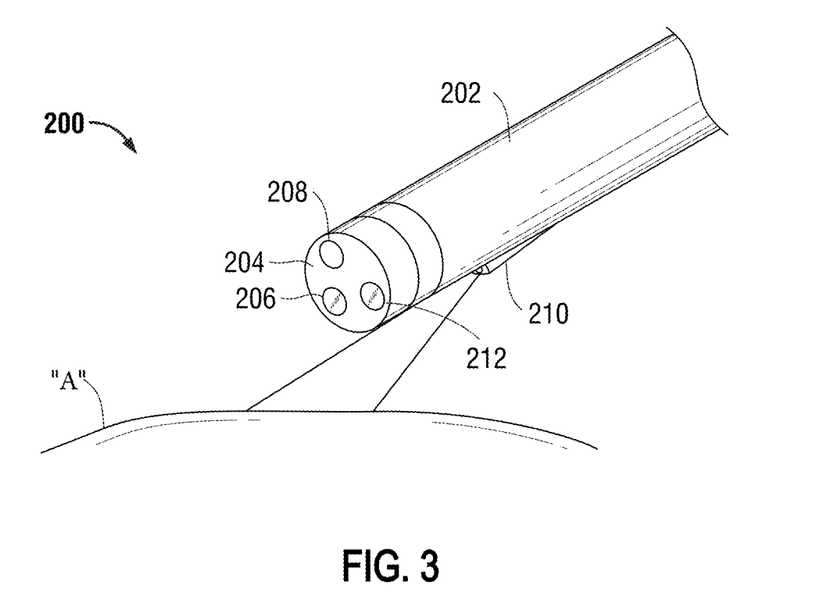
FIG. 3 is a front, perspective view, of a distal portion of the 3D endoscope of FIG. 1 illustrating the 3D endoscope positioned relative to the anatomy of a patient.

FIGS. 1-3 illustrate a system for generating a 3D model and enhanced surgical navigation in accordance with the disclosure and is generally described as system 100. System 100 includes a computing device 150 and a 3D endoscope 200 configured to scan and image a surgical site "S" of a patient "P". The 3D endoscope 200 is coupled to the computing device 150 and any of the 3D endoscope 200, the computing device 150, or the two in cooperation, is configured to generate a 3D model of the surgical site "S".

The 3D endoscope 200 includes an elongate body 202 configured to be advanced within a suitable thoracic trocar (not shown) or other device capable of penetrating the chest wall and receiving an endoscope or a thoracic catheter therethrough to access the thoracic cavity. The 3D endoscope 200 may be positioned in close proximity to the chest wall to navigate the shallow portions of the surgical site "S" (e.g., the thoracic cavity) between the lungs or other anatomy "A" (FIG. 1) and the chest wall of the patient "P". As can be appreciated, the elongate body 202 may include any number of movable segments to aid in the maneuverability of the 3D endoscope 200 within the surgical site "S" (e.g., the thoracic cavity).

The 3D endoscope 200 includes an optical camera 206, a light source 208, a scanner 210 (e.g., structured light projection source, structured light scanner, laser, etc.), and a second camera 212 (also referred to herein as a "camera source").

The optical camera 206 is a visual-light optical camera, such as a charge-coupled device (CCD), complementary metal-oxide-semiconductor (CMOS), N-type metal-oxide-semiconductor (NMOS), or other suitable camera known in the art. In one non-limiting embodiment, the optical camera 206 is a CCD camera having a resolution of 1080p. The light source 208 is a light emitting diode (LED) emitting white light, although any light emitting device known in the art may be utilized.

The scanner 210 may be any structured light scanner known in the art, such as an LED or LED infrared (IR) laser that is dispersed into a scan pattern (line, mesh, dots, or combinations thereof), by rotating mirror, beam splitter, diffraction grating, or panning of the scanner 210 itself. As can be appreciated, the scanner 210 may employ infrared light so as to avoid interference from visible light sources, although it is contemplated that the scanner 210 may emit light in the visible spectrum, or any other wavelength, depending upon the tissue being scanned during the procedure. The scanner 210 includes a known position relative to a camera and permits the calculation of the exact location of the intersection between the light ray from the scanner 210 and the camera. This information can be scanned as single points, lines, or arrays to create topologic maps of surfaces. In one non-limiting embodiment, the scanner 210 may be a LED laser having collimated light. The scanner 210 (e.g., laser scanner, structured light source, etc.) will enable visualization systems to achieve accurate surface maps of the lung (or other anatomy) needed in order to match preoperative computed images (or image data acquired by a camera, for example, optical camera 206 or second camera 212 of the 3D endoscope 200) to the operative image delivered to the endoscopic camera.

The scanner 210 cooperates with the second camera 212 such that the second camera 212 acquires images of the scan pattern projected by the scanner 210 as the scanner 210 pans a projection along the surface of the surgical site.

The second camera 212 is a CCD camera capable of detecting reflected IR light, although it is contemplated that the second camera 212 may detect visible light, such as visible green light or the like, depending upon the tissue being scanned. Specifically, visible green light contrasts with tissue having a red or pinkish hue enabling the second camera 212 to more easily identify the topography of the tissue. A digital filter (not shown) or a filter having narrow band optical grating (not shown) inhibits extraneous visible light emitted from the scanner 210 from distracting the surgeon during the surgical procedure. In embodiments, the visible light is filtered from the image captured by the optical camera 206 and transmitted to the surgeon such that the image is clear and free from extraneous light patterns.

It is contemplated that the second camera 212 may be any thermographic camera known in the art, such as such as ferroelectric, silicon microbolometer, or uncooled focal plane array (UFPA), or may be any other suitable visible light camera such as a charge-coupled device (CCD), complementary metal-oxide-semiconductor (CMOS), N-type metal-oxide-semiconductor (NMOS), or other suitable camera known in the art where the light emitted from the scanner 210 is in the visible or detectable spectrum. In embodiments, the distal surface 204 may include a suitable transparent protective cover (not shown) capable of inhibiting fluids or other contaminants from coming into contact with each of the optical camera 206, light source 208, scanner 210, and second camera 212. Since the distance between the scanner 210 and second camera 212 relative to the optical camera 206 is fixed, the images obtained by the optical camera 206 can more accurately be matched with a pre-operative image and/or intra-operative image, as will be described in further detail hereinbelow.

In embodiments, the scanner 210 may be disposed on a distal portion of the 3D endoscope 200. As can be appreciated, the location of the scanner 210 on the distal portion of the 3D endoscope 200 enables triangulation where the scanner 210 and second camera 212 are directed at an angle from the centerline of the distal portion of the 3D endoscope 200 (e.g., the scanner 210 and second camera 212 are disposed at an angle incident to a longitudinal axis defined by the distal portion of the 3D endoscope 200).

In operation, initially, the patient "P" (FIG. 1) may be imaged using any suitable imaging device (not shown), such as MRI, ultrasound, CT scan, Positron Emission Tomography (PET), or the like, and the images are stored within a memory (not shown) coupled to computing device 150. The memory may include any non-transitory computer-readable storage media for storing data and/or software that is executable by a processor (not shown) e.g., solid-state, volatile, non-volatile, removable, and non-removable.

After the patient "P" is imaged, the clinician penetrates the chest of a patient "P" using a trocar (not shown) or other suitable device. The distal portion of the 3D endoscope 200 is advanced within the trocar, and thereafter, within the surgical site "S" (e.g., the thoracic cavity) of the patient "P" (FIG. 2). As the 3D endoscope 200 is further advanced within the thoracic cavity, the clinician observes the images obtained by the optical camera 206 on a display (not shown). Once facing the surface of the anatomy "A", for example the lung "L" (e.g., incident the lung surface), the scanner 210 emits IR light and pans the IR light along the surface of the anatomy "A" or surgical site "S", which is reflected off the surface of the anatomy "A" and detected by the second camera 212. The 3D endoscope 200 may be advanced over the surface of the anatomy "A" in a caudal, cephalad, or lateral direction, or combinations thereof. The data obtained by the second camera 212 is processed (for example, by the computing device 150) to generate a 3D model of the surface of the surgical site "S" including the anatomy "A" and any objects present therein, such as surgical tools, using any suitable means, such as stitching, warping, or the like. The 3D endoscope 200 may be advanced over the entire surface of the anatomy "A" in order to obtain as complete a map as possible.

The light source 208 and the optical camera 206 may be simultaneously operated with the scanner 210 and second camera 212 to permit correlation of the images received from the optical camera 206 with previously acquired pre-operative images. The correlation between the images obtained by the optical camera 206 and the previously acquired preoperative images permits more accurate mapping of the surface of the anatomy "A" and the surgical site "S". As can be appreciated, the accuracy of the correlation may be further improved using tracking software to track the distal tip of the 3D endoscope 200.

Figure 4:
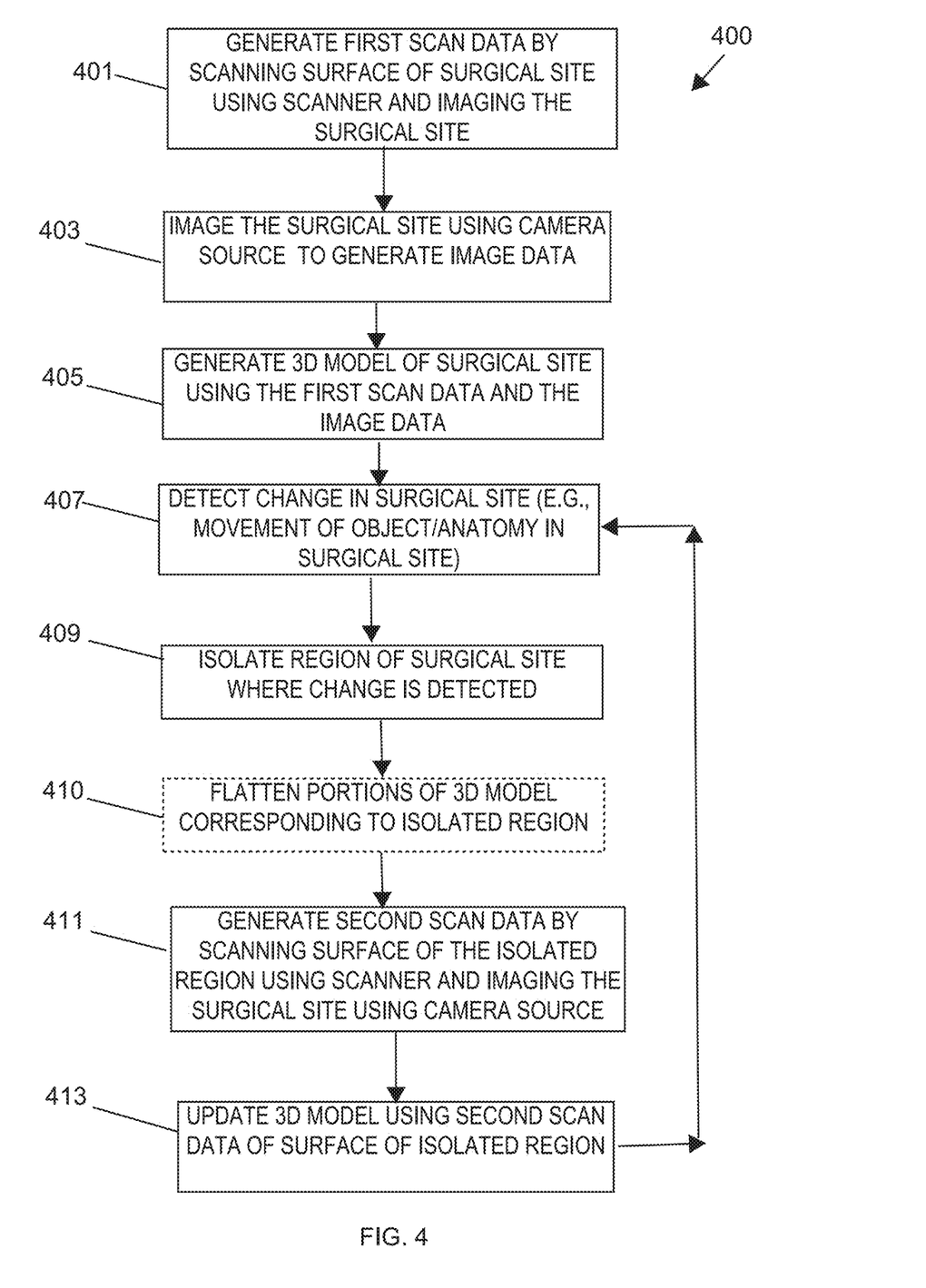
FIG. 4 is a flowchart illustrating a method for generating a 3D model of a surgical site in accordance with an aspect of the disclosure.

FIG. 4 illustrates a flow chart of a method for generating a 3D model of a surgical site using system 100 or its components and is described as method 400. The steps of method 400, although described in a particular order, may be performed in any order not specifically described. Additionally, or alternatively, although method 400 is described as including the steps described, method 400 may include some or all of the steps described. Some or all of the steps of method 400 may be carried out, partially or fully, by any single component of system 100, or alternatively, may be carried out partially or fully by a combination of components of system 100. For example, some of the steps of method 400 may be carried out by 3D endoscope 200 while others may be carried out by computing device 150.

Figure 5A:
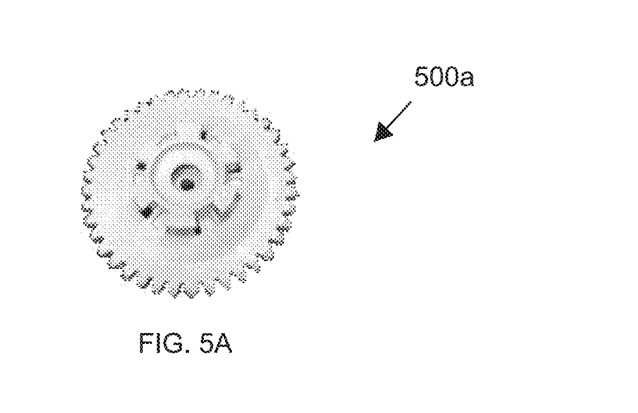
FIG. 5A illustrates an object to be scanned by a scanner of the 3D endoscope of FIG. 1.
Figure 5B:
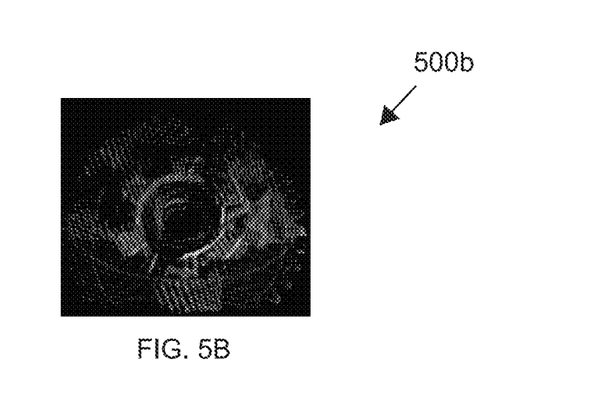
FIG. 5B illustrates the resulting scan data of the object of FIG. 5A.

Method 400 begins at step 401 where a surface of a surgical site is scanned using a scanner (e.g. scanner 210) and the surgical site is imaged using a camera source (e.g., optical camera 206 and/or second camera 212) to generate first scan data. In an aspect, the first scan data is a scanned model of the object scanned. For example, FIG. 5A illustrates an object 500a to be scanned by a scanner and imaged by a camera source and FIG. 5B illustrates the resulting scan data 500b (e.g., first scan data) of the object scanned. In an aspect, the scanner 210 pans an IR projection along the surface of the surgical site and the reflected IR projections detected in the images of the scanned surface are used to generate the first scan data. In particular, the scanner 210 pans an IR projection along the surface of the surgical site and the second camera 212 simultaneously acquires images of the surgical site (including the reflection of the IR projection from the scanner 210 onto the surface of the surgical site) and the first scan data is generated based on the panned projection as it is reflected off of the surface of the surgical site or object scanned.

Figure 5C:
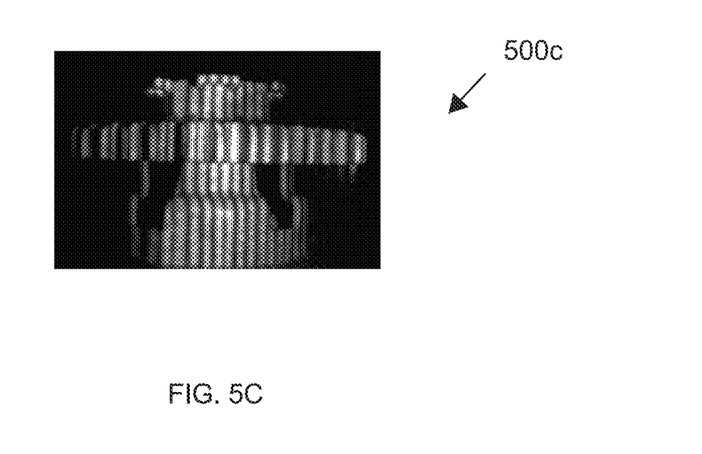
FIG. 5C illustrates a 3D model of the object of FIG. 5A.

In step 403, the surgical site is imaged using a camera source (e.g., optical camera 206, second camera 212, or both) to generate image data. As noted above, this image data may also include the panned pattern projected along the surgical site by the scanner 210. In an aspect, the images used in step 401 for generating the first scan data are the same as the images acquired in step 403. In step 405, a 3D model of the surgical site is generated using the first scan data generated in step 401 and the image data acquired in step 403. For example, FIG. 5C illustrates a 3D model 500c of the object 500a (FIG. 5A) scanned by scanner and imaged by camera source.

In an aspect, the generating of the 3D model in step 405 is accomplished by warping the image data onto the scanned model (e.g., the scan data). The scanner used for generating the first scan data may be incorporated into the same device (e.g., 3D endoscope) as the camera source for generating the image data, or alternatively may be a separate device. In an aspect, the 3D model includes a matrix of equidistant data points representing fixed points in a current view of the surgical site and a value of a data point represents an existence of an object at the data point in space.

As described above, the surgical site may include objects that move during the scanning, imaging, and generating of the 3D model. For example, when imaging an anatomy, such as a lung, breathing or other natural and unnatural movements, may cause the anatomy or lung to change shape. Therefore, in certain instances, when the object moves, the resulting 3D model is skewed or otherwise inaccurate. To address this issue, and to speed up the 3D reconstruction process, method 400 includes step 407-413, described in detail below.

In step 407, a determination is made that a change is detected in the surgical site. In an aspect, in step 407, image processing is performed on real-time image data captured by the camera source (e.g., second camera 212) and a determination is made as to whether an object (e.g., anatomy) has moved within the surgical site. In particular, step 407 may include comparing an image of a portion of the surgical site captured by the camera source at a time t with an image of the portion of the surgical site captured by the camera source at a time t−1, and determining that there exists a change in the surgical site if the image captured at time t is different from the image captured at time t−1. Additionally, or alternatively, processing may be performed on scan data generated using a scan source (e.g., scanner 210) and a camera source (e.g., second camera 212). For example, step 407 may include comparing scan data of a portion of the surgical site at a time t with scan data of the portion of the surgical site at a time t−1, and determining that there exists a change in the surgical site if the scan data at time t is different from the scan data at time t−1. In an aspect, step 407 includes a combination of analysis of both of the scan data and the image data, over a period of time, to make the determination that a change is detected in the surgical site. Additionally, the determination made in step 407 may be a function of data (e.g., image data) retrieved from an external source, separate from a 3D endoscope, for example a difference camera source of motion sensors fixed to the patient.

In certain aspects, a user may want to ignore movement of certain objects within the surgical site, which would otherwise trigger a detection in step 407. To this end, a user may select, or the system may automatically detect, certain objects within the surgical site where the movement of which would be ignored. For example, the presence of a surgical tool within the 3D endoscope's field of view can be ignored, thereby not triggering a detected change in step 407, or the movement of a part of the anatomy not intended to be reconstructed in 3D can be ignored.

In step 409, the region of the surgical site where the change is detected (from step 407) is isolated. For example, the portion of the surgical site or the portion of the object in the surgical site that moved, thereby causing the detected change, is isolated. Method 400 may also include step 410, where portions of the 3D model that correspond to the isolated region are flattened. As described above, when the surface being scanned, or an object in the surgical site, moves more rapidly than the scan time, the resulting 3D model is inaccurate and may appear similar to a blurred photograph. Thus, in step 410, in order to prevent loss of visual context, the 3D model is flattened in the changed area(s) until such a time that a scan of the area can be completed, and the map can be updated. Such a step may be performed conditionally, for example, when the area of change between two consecutive images exceeds what can be scanned without notice by the user.

In step 411, the isolated region is scanned to generate second scan data. In particular, in step 411, second scan data corresponding to only the isolated region is generated by scanning the isolated region and imaging the surgical site. In an aspect, the scanner 210 pans an IR projection along the surface of the isolated region of the surgical site and the reflected IR projections detected in the images of the scanned surface are used to generate the second scan data. In particular, the scanner 210 pans an IR projection along the surface of the isolated region of the surgical site and the second camera 212 simultaneously acquires images of the surgical site (including the reflection of the IR projection from the scanner 210 onto the surface of isolated region) and the second scan data is generated based on the panned projection as it is reflected off of the surface of the surgical site or object scanned.

In an aspect, step 411 includes using the same scanner, or a different scanner, then that which was used to generate the first scan data in step 401. In an aspect, step 411 includes scanning the surface of the isolated region using the scanner for generating second scan data by reducing a field of view of the scanner to match the isolated region. In this manner, the region scanned by the scanner is restricted to the isolated region, or in other words, regions that have been determined to have a moving object or moving portion.

In step 413, the 3D model generated in step 405 is updated using the second scan data of the isolated region generated in step 411. To this end, the resulting updated 3D model of the surgical site, or objects therein, is updated in real-time upon detection of a change in the surgical site. Additionally, or alternatively, the step of updating the 3D model in step 413 may replace the step of generating the 3D model (step 405) entirely, in that, the 3D model is only partially generated in step 405 and completed in step 413, thereby reducing processing speeds and accounting for movement of objects in the surgical site. In an aspect, the updated 3D model includes a matrix of equidistant data points representing fixed points in a current view of the surgical site and a value of a data point represents an existence of an object at the data point in space. Upon completion of step 413, or before completion of step 413 (for example, upon detecting another change/movement in the surgical site), method 400 may revert back to step 407.

The 3D model generated in method 400, and the updated 3D model generated in method 400, may be displayed on a display of computing device 150 or another component of system 100 via one or more graphical user interfaces.

In addition to the above-described methods performable by system 100, system 100 may detect coordinate mismatches and notify the user or modify the display of the graphical user interface based on the detected mismatch. The anatomy being scanned is not static and will change over time due to elements such as manipulation by the surgeon, natural biological rhythms (e.g. cardiac, pulmonary), and gravity. Detection of such changes by system 100 can include three-dimensional coordinate mismatches between current scanned locations of objects in the current field of view and those from a previous view (e.g., a surface that extends out of the current view where the Y coordinates of the surface in view differs from that outside).

Previously scanned structures completely outside of the current view may change as well. In an aspect, system 100 indicates to the user that all items outside the current field of view may have changed. To this end, system 100 may modify the displayed image of all elements outside the current field of view via blurring, removing three-dimensional effects (e.g., flattening the image), and removal of color or fading of color. Additionally, or alternatively, the items within the field of view may continue to be updated in real-time by system 100.

In particular applications, the 3D endoscope 200 position, or its individual components, will also be tracked by an intraoperative instrument tracking system, such as electromagnetic tracking systems. The locational information obtained by the intraoperative instrument tracking system aids in simplifying the algorithms needed to produce large-scale spatial surface maps from segmental sized scans taken from an endoscope. Further, this immediate intraoperative guidance of the optical image location to the surface map and preoperative computed images provides even greater clarity of location and orientation of the endoscope.

In some embodiments, the 3D endoscope 200 is positionable by a robotic system. The robotic system provides precise six-axis orientation of the endoscope in a similar manner to an intraoperative navigation system but benefited by active positioning as well as locational knowledge of the endoscope within the patient. As can be appreciated, the robotic system may be utilized to autonomously move the endoscope to complete scans of larger areas or whole organs.

In particular, surgical instruments such as the endoscopes, computing devices, and other components of system 100 described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

It is contemplated that the endoscopes described herein may be positioned by the robotic system and the precise position of the endoscope transmitted to the computer to construct the 3D image of the scanned organ or operative field. The robotic system has the ability to autonomously scan the surgical field and construct a complete 3D model of the field to aid the surgeon in directing the robotic arms or to provide necessary 3D information for the robotic system to further conduct surgical steps autonomously. In embodiments, where the endoscope includes a camera and a structured light source that are independent of one another, the robotic system may direct the camera and a structured light source separately. The robotic system provides the relative coordinates between respective endoscopes needed to triangulate the points in the structured light and camera views to construct a 3D surface of the operative field. In this manner, the robotic system has a specific advantage of being able to autonomously position the structure light source onto the field of view of the camera or camera endoscope. Additionally, or alternatively, with the robot controlling the camera location (or other component location), the robot may move the camera (or other component) to expand the size of the scanned anatomy (e.g., the amount scanned) to create a larger view for the user (e.g., surgeon) without input or knowledge by the user.

Figure 6:
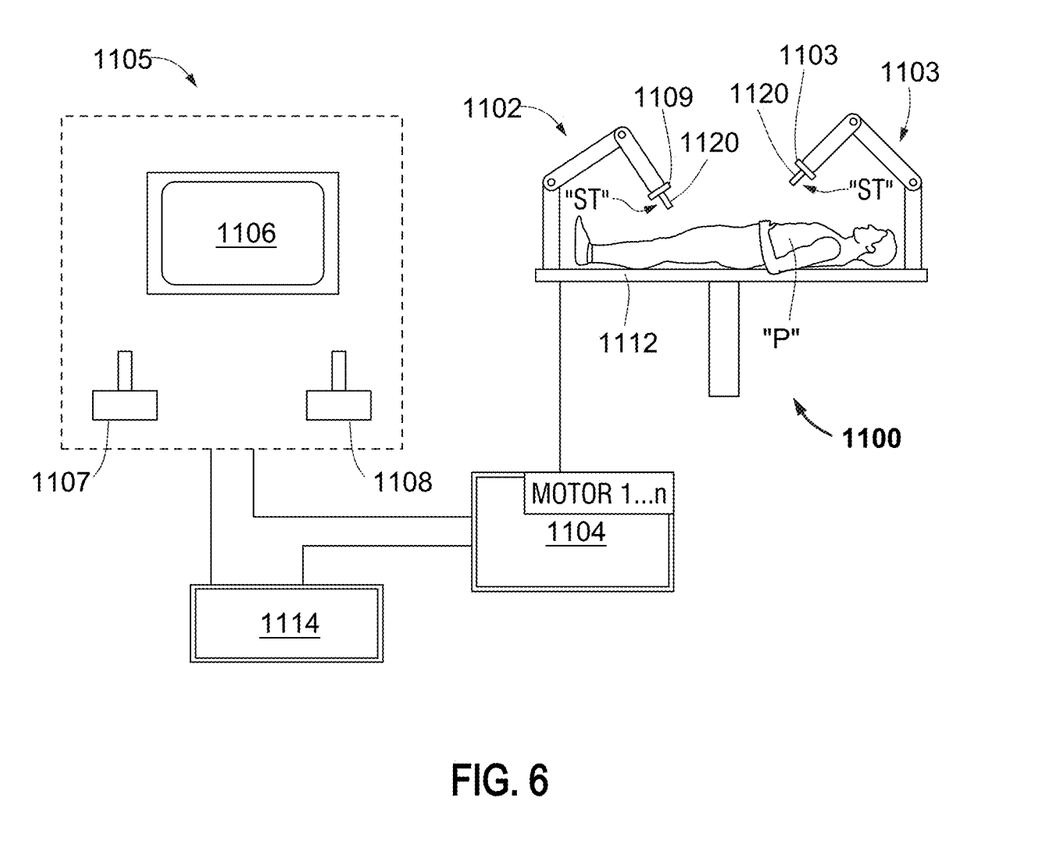
FIG. 6 is a schematic illustration of a robotic surgical system configured for use in accordance with the disclosure.

FIG. 6 illustrates a medical workstation 1100 including a plurality of robot arms 1102, 1103, a control device 1104, and an operating console 1105 coupled with control device 1104. Operating console 1105 may include a display device 1106, which may be set up in particular to display 3D images, and manual input devices 1107, 1108, by means of which a person (not shown), for example a surgeon, may be able to telemanipulate robot arms 1102, 1103.

Each of the robot arms 1102, 1103 may include a plurality of members, which are connected through joints, and an attaching device 1109, 1111, to which may be attached, for example, a surgical tool "ST" (e.g., 3D endoscope 200) supporting an end effector 1120, in accordance with any one of several embodiments disclosed herein, as will be described in greater detail below.

Robot arms 1102, 1103 may be driven by electric drives (not shown) that are connected to control device 1104. Control device 1104 (e.g., a computer) may be set up to activate the drives, in particular by means of a computer program, in such a way that robot arms 1102, 1103, their attaching devices 1109, 1111 and thus the surgical tool (including end effector 1120) execute a desired movement according to a movement defined by means of manual input devices 1107, 1108. Control device 1104 may also be set up in such a way that it regulates the movement of robot arms 1102, 1103 and/or of the drives.

Medical workstation 1100 may be configured for use on a patient "P" lying on a patient table 1112 to be treated in a minimally invasive manner by means of end effector 1120.

Medical workstation 1100 may also include more than two robot arms 1102, 1103, the additional robot arms likewise being connected to control device 1104 and being telemanipulatable by means of operating console 1105. A medical instrument or surgical tool (including an end effector 1120) may also be attached to the additional robot arm. Medical workstation 1100 may include a database 1114, in particular coupled to with control device 1104, in which are stored, for example, pre-operative data from patient/living being "P" and/or anatomical atlases.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments.

As used hereinabove, the term "clinician" refers to a doctor, a nurse, or any other care provider and may include support personnel. Throughout this description, the term "proximal" refers to the portion of the device or component thereof that is closer to the clinician and the term "distal" refers to the portion of the device or component thereof that is farther from the clinician. Additionally, in the drawings and in the description above, terms such as front, rear, upper, lower, top, bottom, and similar directional terms are used simply for convenience of description and are not intended to limit the disclosure. In the description hereinabove, well-known functions or constructions are not described in detail to avoid obscuring the disclosure in unnecessary detail.

What is claimed is:

1. A method for generating a 3D model of a surgical site comprising:
   generating first scan data based on reflected IR projections projected onto a surface of the surgical site using a scanner and a camera source;
   generating a 3D model of the surgical site using the first scan data and image data of the surgical site;
   detecting a change in the surgical site during the generation of the first scan data, the change resulting in an inaccuracy of the 3D model;
   isolating a region of the surgical site where the change is detected;
   displaying the 3D model with portions of the 3D model corresponding to the isolated region flattened;
   generating second scan data of only the isolated region based on reflected IR projections projected onto the isolated region using the scanner and the camera source, wherein a field of view of the second scan data is reduced to match the isolated region;
   updating the 3D model generated using the second scan data of the surface of the isolated region; and
   displaying the updated 3D model on a display.

2. The method of claim 1, wherein detecting the change in the surgical site includes detecting movement of an object in the surgical site.

3. The method of claim 1, wherein detecting the change in the surgical site includes:
   comparing an image of a portion of the surgical site captured by the camera source at a time t with an image of the portion of the surgical site captured by the camera source at a time t−1; and
   determining that there exists the change in the surgical site when the image captured at time t is different from the image captured at time t−1.

4. The method of claim 1, wherein detecting the change in the surgical site includes:
   comparing scan data of the portion of the surgical site at a time t with scan data of the portion of the surgical site at a time t−1; and
   determining that there exists the change in the surgical site when the scan data at time t is different from the scan data at time t−1.

5. The method of claim 1, wherein:
   generating first scan data based on reflected IR projections projected onto the surface of the surgical site using the scanner and the camera source includes using a scanner and a camera source of a 3D endoscope.

6. The method of claim 1, wherein generating the 3D model of the surgical site using the first scan data and the image data includes warping the image data onto the first scan data.

7. A system for generating a 3D model of a surgical site comprising:
   a 3D endoscope including a camera source and a scanner; and
   a computing device operably coupled to the 3D endoscope and configured to:
   generate a 3D model of a surgical site using scan data and image data acquired by the 3D endoscope;
   detect a change in the surgical site during the acquisition of the scan data, the change resulting in an inaccuracy of the 3D model;
   isolate a region of the surgical site where the change is detected;
   display the 3D model with portions of the 3D model corresponding to the isolated region flattened;
   cause the scanner to scan a surface of only the isolated region to generate second scan data of the isolated region, wherein a field of view of the second scan data is reduced to match the isolated region; and
   update the 3D model generated using the second scan data of the isolated region.

8. The system of claim 7, wherein the computing device is further configured to:
   display the updated 3D model.

9. The system of claim 7, wherein the computing device detects a change in the surgical site by detecting movement of an object in the surgical site.

10. The system of claim 7, wherein the computing device detects the change in the surgical site by:
    comparing an image of a portion of the surgical site captured by the camera source at a time t with an image of the portion of the surgical site captured by the camera source at a time t−1; and
    determining that there exists the change in the surgical site when the image captured at time t is different from the image captured at time t−1.

11. The system of claim 7, wherein the computing device detects the change in the surgical site by:
    comparing scan data of a portion of the surgical site at a time t with scan data of the portion of the surgical site at a time t−1; and
    determining that there exists the change in the surgical site when the scan data at time t is different from the scan data at time t−1.

12. The system of claim 7, wherein the computing device generates the 3D model of the surgical site by warping the image data onto the scan data.

13. The system of claim 7, wherein the 3D model includes a matrix of equidistant data points representing fixed points in a current view of the surgical site and a value of a data point represents an existence of an object at the data point in space.

14. A non-transitory computer-readable storage medium encoded with a program that, when executed by a processor, causes the processor to:
generate a 3D model of a surgical site using scan data and image data;
scan a surface of an isolated region of the surgical site corresponding to a portion of the surgical site that has changed to generate second scan data;
detect a change in the surgical site during the scan, the change resulting in an inaccuracy of the 3D model;
isolate a region of the surgical site where the change is detected;
display the 3D model with portions of the 3D model corresponding to the isolated region flattened;
scan a surface of only the isolated region to generate second scan data of the isolated region, wherein a field of view of the second scan data is reduced to match the isolated region; and
update the 3D model generated using the second scan data.

15. The non-transitory computer-readable storage medium of claim 14, wherein the program, when executed by the processor, further causes the processor to detect a change in the surgical site by detecting movement of an object in the surgical site.

16. The non-transitory computer-readable storage medium of claim 14, wherein the program, when executed by the processor, further causes the processor to:
detect the change in the surgical site by:
comparing an image of a portion of the surgical site captured by a camera source at a time t with an image of the portion of the surgical site captured by the camera source at a time t−1; and
determining that there exists the change in the surgical site when the image captured at time t is different from the image captured at time t−1.

17. The non-transitory computer-readable storage medium of claim 14, wherein the program, when executed by the processor, further causes the processor to:
detect the change in the surgical site by:
comparing scan data of a portion of the surgical site at a time t with scan data of the portion of the surgical site at a time t−1; and
determining that there exists the change in the surgical site when the scan data at time t is different from the scan data at time t−1.

* * * * *